US011885819B2

(12) United States Patent
Takiwaki et al.

(10) Patent No.: US 11,885,819 B2
(45) Date of Patent: *Jan. 30, 2024

(54) ANALYSIS METHOD OF DIENE COMPOUND

(71) Applicants: JEOL Ltd., Tokyo (JP); TOKUYAMA CORPORATION, Yamaguchi (JP)

(72) Inventors: Masaki Takiwaki, Tokyo (JP); Seketsu Fukuzawa, Tokyo (JP); Misao Matsushige, Yamaguchi (JP); Shin Watanabe, Yamaguchi (JP)

(73) Assignees: JOEL LTD, Tokyo (JP); TOKUYAMA CORPORATION, Yamaguchi (JP)

( * ) Notice: Subject to any disclaimer, the term of this patent is extended or adjusted under 35 U.S.C. 154(b) by 559 days.

This patent is subject to a terminal disclaimer.

(21) Appl. No.: 17/065,221

(22) Filed: Oct. 7, 2020

(65) Prior Publication Data

US 2021/0109119 A1    Apr. 15, 2021

(30) Foreign Application Priority Data

Oct. 9, 2019  (JP) ................................ 2019-186259

(51) Int. Cl.
*G01N 33/82* (2006.01)
*G01N 30/06* (2006.01)
*C07D 487/08* (2006.01)

(52) U.S. Cl.
CPC .......... *G01N 33/82* (2013.01); *C07D 487/08* (2013.01); *G01N 30/06* (2013.01); *G01N 2030/067* (2013.01); *G01N 2560/00* (2013.01)

(58) Field of Classification Search
CPC ........................ G01N 33/82; G01N 2030/067
See application file for complete search history.

(56) References Cited

U.S. PATENT DOCUMENTS

| | | |
|---|---|---|
| 2011/0301063 A1 | 12/2011 | Netzel et al. |
| 2018/0088137 A1 | 3/2018 | Higashi et al. |
| 2018/0136240 A1 | 5/2018 | Higashi et al. |
| 2021/0253587 A1* | 8/2021 | Seki .................... C07D 487/08 |

FOREIGN PATENT DOCUMENTS

| | | | |
|---|---|---|---|
| EP | 3301453 A1 | 4/2018 | |
| JP | 201881023 A | 6/2011 | |
| JP | 2015166740 A | 9/2015 | |
| JP | 2018054459 A | 4/2018 | |
| WO | WO-2019240143 A1 * | 12/2019 | ........... C07D 487/04 |

OTHER PUBLICATIONS

Seki, M. et al. "A novel caged Cookson-type reagent toward a practical vitamin D derivatization method for mass spectrometric analyses," Rapid Commun Mass Spectrom. 2020;34:e8648. First published Nov. 12, 2019; including supporting information (Year: 2019).*
Kiselev, V.D. et al. "Features of the Diels-Alder Reaction between 9,10-Diphenylanthracene and 4-Phenyl-1,2,4-triazoline-3,5-dione," Russian Journal of Physical Chemistry A, 2014, vol. 88, No. 12, pp. 2073-2080 (Year: 2014).*
Kiselev, V.D. et al. "Why can the Diels-Alder reaction of 9,10-diphenylanthracene with 4-phenyl-1,2,4-triazoline-3.5-dione pass by an abnormal way?" Mendeleev Commun., 2013, 23, 235-236 (Year: 2013).*
Roy, N. et al. "Dynamic Covalent Chemistry: A Facile Room-Temperature, Reversible, Diels-Alder Reaction between Anthracene Derivatives and N-Phenyltriazolinedione," Chem. Asian J. 2011, 6, 2419-2425, including supporting information (Year: 2011).*
Kiselev, V.D. et al. "Kinetic and equilibrium parameters of [4+2] cycloaddition reaction of 2,6-dimethylnaphthalene with 4-phenyl-1,2,4-triazoline-3,5-dione," Russian Chemical Bulletin, International Edition, vol. 63, No. 3, pp. 770-771, Mar. 2014 (Year: 2014).*
S. Ogawa, et al., "A Novel Cookson-Type Reagent for Enhancing Sensitivity and Specificity in Assessment of Infant Vitamin D Status Using Liquid Chromatography/Tandem Mass Spectrometry," Rapid Commun. Mass Spectrom. 2013; 27, 2453-2460.
S. Ogawa, et al., "Comparative Evaluation of New Cookson-Type Reagents for LC/ESI-MS/MS Assay of 25-Hydroxyvitamin D3 in Neonatal Blood Samples," Biomed. Chromatogr. 2016; 30, 938-945.
S. Ogawa, et al., "Enhancing Analysis Throughput, Sensitivity and Specificity in LC/ESI-MS/MS Assay of Plasma 25-Hydroxyvitamin D3 by Derivatization With Triplex 4-(4-Dimethylaminophenyl)-1,2,4-Triazoline-3,5-Dione (DAPTAD) Isotopologues," Journal of Pharmaceutical and Biomedical Analysis 136, 2017; 126-133.
K.D. Bruycker, et al., "Triazolinediones as Highly Enabling Synthetic Tools," Chemical Reviews, 116, 2016; 3919-3974.
Ford Jackson W., et al., "Solvent Effects on the Kinetics of a Diels-Alder Reaction in Gas-Expanded Liquids", Industrial & Engineering Chemistry Research, 2008, vol. 47 (3), p. 632-637.
Werner Stefan, et al., "Fluorous Dienophiles Are Powerful Diene Scavengers in Diels-Alder Reactions", Organic Letters, 2003, vol. 5 (18), p. 3293-3296.

(Continued)

*Primary Examiner* — Jennifer Wecker
*Assistant Examiner* — Michelle Adams
(74) *Attorney, Agent, or Firm* — HOGAN LOVELLS US LLP

(57) ABSTRACT

Provided is a method for analyzing a diene compound including: a triazolinedione adduct heating step of heating a triazolinedione adduct to produce a triazolinedione compound; an ene compound formation step of reacting the triazolinedione compound with a diene compound to obtain an ene compound; and an ene compound analysis step of analyzing the ene compound to quantitative determine the diene compound. Also provided is a method for producing an ene compound, including: a triazolinedione adduct heating step of heating a triazolinedione adduct to produce a triazolinedione compound; and an ene compound formation step of reacting the triazolinedione compound with a diene compound to obtain an ene compound.

14 Claims, No Drawings

(56) References Cited

OTHER PUBLICATIONS

Mallakpour Shadpour E., et al., "Synthesis of New Heterocyclic Compounds via Cycloaddition Reaction", Indian Journal of Chemistry, Section B: Organic Chemistry Including Medicinal Chemistry, 2002, vol. 41B (4), p. 812-816.
Thompson R. Lee, et al., "Rate Variations of a Hetero-Diels-Alder Reaction in Supercritical Fluid CO2", Industrial & Engineering Chemistry Research, 1999, vol. 38 (11), pp. 4220-4225.
Angermund Klaus, et al., "Thermal and Photochemical Reactions of Naphtho[L,2,3,4-DEF] chrysene with 4-Phenyl-1,2,4-triazol ine-3,5-dione", Chemische Berichte, 1988, vol. 121 (9), pp. 1647-1650.
Klobucar W. Dirk, et al., "Thermal Retrograde [2+2] Aromatization of Caged Bicyclo[4. 2.0]octa-2,4-diene Derivatives", Journal of Organic Chemistry, 1981, vol. 46 (13), pp. 2680-2683.
Burrage Martin E., et al., "Substituent and Solvent Effects on the Diels-Alder Reactions of Triazolinediones", Journal of the Chemical Society, Perkin Transactions 2: Physical Organic Chemistry, 1975, vol. 12, pp. 1325-1334.
Meehan Scott, et al., "A New Synthesis of Diazenes(Azoalkanes) Using 4-(S,S-Dimethylsulfoximino)-1,2,4-triazoline-3,5-dione. The Construction of Diazenes from Amino Nitrenes via Base-Induced Sulfoximine Cleavage", Journal of Organic Chemistry, 1997, vol. 62 (11), pp. 3779-3781.
Sauer Juergen, et al., "Diels-Alder Reactions. VIII. 4-Phenyl-1,2,4-triazoline-3,5-dione as a Dienophile", Chemische Berichte, 1967, vol. 100 (2), pp. 678-684.
Shimada, Kazutake et al., "High-performance liquid chromatography/ mass spectrometry of vitamin D compounds employing derivatization with Cookson-type reagents", Bunseki Kagaku, 2002, vol. 51 No. 7, pp. 487-493 (2002).
Cookson, Richard C. et al., "Diels-Alder reactions of 4-Pheny 1-1, 2, 4-triazoline-3, 5-dione", Journal of the Chemical Society [Section] C: Organic, 1967, vol. 19, pp. 1905-1909.
Fernandez-Herrera, Maria A. et al., "A Convenient Methodology for the in situ Oxidation of 4-Substituted Urazoles. Setting up a One-Pot Procedure for the Efficient Protection of Dienes", Heterocycles, 2013, vol. 87 (3), pp. 571-582.
Chatani, Hitoshi et al., "Contribution of the Proton Affinity in Cookson-Type Reagents Pretreating the Analytes to Improve the Detection Efficiency of Steroid Derivatives in ESI/MS Analysis", The 10th Annual meeting of Japan Society for Molecular Science, Lecture program abstracts, Aug. 31, 2016, 3P098.
Menard Cecilia, et al., Ph3BiC03. "A Mild Reagent for in situ Oxidation of Urazoles to Triazolinediones", Tetrahedron Letters, 2003, vol. 44 (35), pp. 6591-6593.

\* cited by examiner

ANALYSIS METHOD OF DIENE COMPOUND

This application is based on and claims the benefit of priority from Japanese Patent Application No. 2019-186259 filed on 9 Oct. 2019, the contents of which is incorporated herein by reference.

BACKGROUND OF THE INVENTION

Field of the Invention

The present invention relates to a method for analyzing a diene compound and a method for producing an ene compound. Specifically, the present invention relates to a diene compound analysis method for analyzing an extremely small amount of a diene compound with high accuracy using a stable triazolinedione adduct, and a method for producing an ene compound which is a derivative of a diene compound.

Related Art

There has recently been an increased need for analysis of vitamin D and vitamin D metabolites in blood. With regard to an analysis method of vitamin D and the vitamin D metabolites, a method has been proposed in which the vitamin D and the vitamin D metabolites are derivatized using a Cookson-type derivatization reagent and subsequently the derivative is analyzed.

Specifically, the Cookson-type derivatization reagent causes a Diels-Alder reaction with a diene compound such as vitamin D extremely rapidly under mild conditions, to give an ene compound quantitatively (see, Nonpatent Documents 1 to 4). Utilizing this reaction characteristic, vitamin D and the like, which are per se difficult to be quantitatively determined, are reacted with the Cookson-type derivatization reagent to convert vitamin D and the like to an ene compound having higher analysis sensitivity, and thereafter the ene compound is analyzed.

Examples of the aforementioned Cookson-type derivatization reagent include triazolinedione compounds such as PTAD (4-phenyl-1,2,4-triazoline-3,5-dione) and DAPTAD (4-(4'-dimethylaminophenyl)-1,2,4-triazoline-3,5-dione).

Non-Patent Document 1: S. Ogawa, et al., Rapid Commun. Mass Spectrom, 27 (2013) 2453-2460
Non-Patent Document 2: S. Ogawa, et al., Biomed. Chromatgr., 30 (2016) 938-945
Non-Patent Document 3: S. Ogawa, et al., J. Pharm. Biomed. Anal., 136 (2017) 126-133
Non-Patent Document 4: K. D. Bruycker, et al., Chem. Rev., 116 (2016) 3919-3974

SUMMARY OF THE INVENTION

However, the triazolinedione compound used as the Cookson-type derivatization reagent is unstable, and higher stability is required for handling as an analysis reagent. Thus, converting the unstable triazolinedione compound to a stable adduct, and regenerating the triazolinedione compound from the stable adduct just before use to react the triazolinedione compound with a diene compound would enable the triazolinedione compound to be used as a highly stable and easy-to-handle analysis reagent for diene compounds.

Typically, the triazolinedione adduct produces the triazolinedione compound upon the application of heat. However, diene compounds including vitamin D3, which are substances to be analyzed, include thermally labile substances. Thus, when a derivatization reaction of the diene compound is carried out using the triazolinedione adduct, measurement sensitivity and accuracy in serving as an analysis reagent are altered depending on analysis conditions, and some use methods of the triazolinedione adduct cause a decrease in measurement sensitivity, and further, in some cases, an inaccurate analysis result is presented.

The present invention has been made in view of the aforementioned related arts, and an object thereof is to provide a method for analyzing a diene compound using the triazolinedione adduct, which enables a derivatization reaction of the diene compound to smoothly proceed by releasing a sufficient amount of triazolinedione compound and inhibiting thermal deterioration of the diene compound, and consequently enables a trace amount of diene compound to be analyzed, and a method for producing an ene compound which is derivatized from a triazolinedione compound.

The present inventors conducted extensive studies for solving the aforementioned problems. Consequently, the present inventors have found that when the triazolinedione adduct is heated to release the triazolinedione compound, and the released triazolinedione compound is reacted with the diene compound, a sufficient amount of triazolinedione compound can be released and deterioration of the diene compound can be prevented, whereby a derivative of the diene compound can be measured while the sensitivity and accuracy required for the analysis of a trace amount of diene compound are sufficiently maintained, to accomplish the present invention.

Specifically, a first aspect of the present invention relates to a method for analyzing a diene compound, including: a triazolinedione adduct heating step of heating a triazolinedione adduct represented by the following formula (1) to produce a triazolinedione compound represented by the following formula (2);

an ene compound formation step of reacting the triazolinedione compound with a diene compound represented by the following formula (3) to obtain an ene compound represented by the following formula (4); and an ene compound analysis step of analyzing the ene compound to quantitatively determine the diene compound,

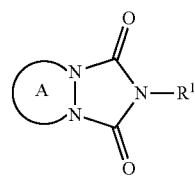

(1)

in which in the formula (1), $R^1$ represents an organic group; and A represents a fused ring having three or more rings including at least one aromatic ring,

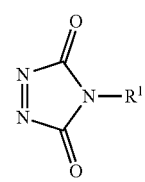

(2)

in which in the formula (2), $R^1$ is as defined in the formula

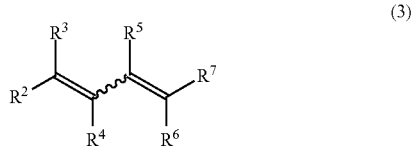

(3)

in which in the formula (3), $R^2$, $R^3$, $R^4$, $R^5$, $R^6$, and $R^7$ each independently represent a group selected from the group consisting of a hydrogen atom, an alkyl group having 1 to 100 carbon atoms, an aralkyl group, a phenyl group, and a heterocyclic group, in which the alkyl group, the aralkyl group, the phenyl group, and the heterocyclic group optionally contain an atom selected from the group consisting of an oxygen atom, a nitrogen atom, a sulfur atom, and a phosphorus atom, and in which at least two of $R^2$, $R^3$, $R^4$, $R^5$, $R^6$, and $R^7$ are optionally combined with one another, and

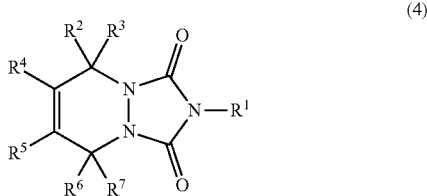

(4)

in which in the formula (4), $R^1$ is as defined in the formula (1); and $R^2$, $R^3$, $R^4$, $R^5$, $R^6$, and $R^7$ are as defined in the formula (3).

$R^1$ in the formula (1) may be a substituted or unsubstituted phenyl group.

$R^1$ in the formula (1) may be a phenyl group having an alkylamino group or an alkylaminoalkyl group.

$R^1$ in the formula (1) may be a phenyl group having a dialkylamino group or a dialkylaminoalkyl group.

The triazolinedione adduct represented by the formula (1) may be a triazolinedione adduct represented by the following formula (5):

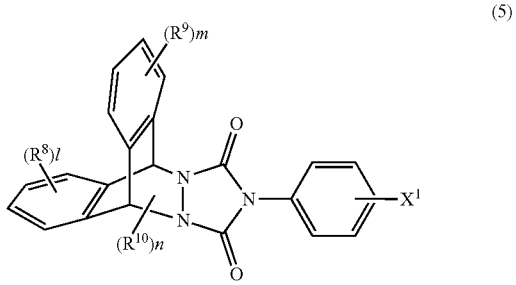

(5)

in which in the formula (5), $X^1$ represents an organic group; $R^8$, $R^9$, and $R^{10}$ each independently represent a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group; l and m are each independently an integer of 0 to 4; and n is an integer of 0 to 2.

$X^1$ in the formula (5) may be an alkylamino group or an alkylaminoalkyl group.

$X^1$ in the formula (5) may be a dialkylamino group or a dialkylaminoalkyl group.

The triazolinedione adduct represented by the formula (1) may be a triazolinedione adduct represented by the following formula (6):

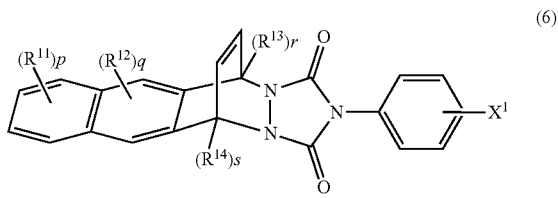

(6)

in which in the formula (6), $X^1$ represents an organic group; $R^{11}$, $R^{12}$, $R^{13}$, and $R^{14}$ each independently represent a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group; p is an integer of 0 to 4; q is an integer of 0 to 2; and r and s are each 0 or 1.

$X^1$ in the formula (6) may be an alkylamino group or an alkylaminoalkyl group.

$X^1$ in the formula (6) may be a dialkylamino group or a dialkylaminoalkyl group.

The diene compound may be a vitamin.

The vitamin may be at least one selected from the group consisting of vitamin D3, 25-hydroxyvitamin D3, 3-epi-25-hydroxyvitamin D3, 24R,25-dihydroxyvitamin D3, vitamin D2, and vitamin A.

The temperature for the heating in the triazolinedione adduct heating step may be 50° C. to 100° C.

The analysis in the ene compound analysis step may be performed by a method using at least one selected from the group consisting of high performance liquid chromatography, high performance liquid chromatography-mass spectrometry (LC-MS), high performance liquid chromatography-tandem mass spectrometry (LC-MS/MS), and mass spectrometry.

Moreover, a second aspect of the present invention relates to a method for producing an ene compound, including: a triazolinedione adduct heating step of heating a triazolinedione adduct represented by the following formula (1) to produce a triazolinedione compound represented by the following formula (2); and an ene compound formation step of reacting the triazolinedione compound with a diene compound represented by the following formula (3) to obtain an ene compound represented by the following formula (4),

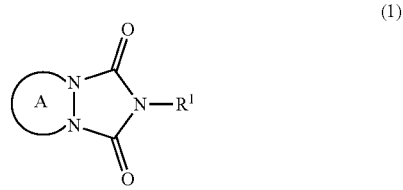

(1)

in which in the formula (1), $R^1$ represents an organic group; and A represents a fused ring having three or more rings including at least one aromatic ring,

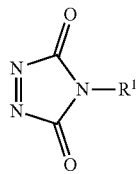

(2)

in which in the formula (2), $R^1$ is as defined in the formula (1),

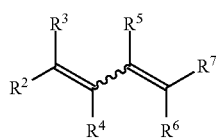

(3)

in which in the formula (3), $R^2$, $R^3$, $R^4$, $R^5$, $R^6$, and $R^7$ each independently represent a group selected from the group consisting of a hydrogen atom, an alkyl group having 1 to 100 carbon atoms, an aralkyl group, a phenyl group, and a heterocyclic group, in which the alkyl group, the aralkyl group, the phenyl group, and the heterocyclic group optionally contain an atom selected from the group consisting of an oxygen atom, a nitrogen atom, a sulfur atom, and a phosphorus atom, and in which at least two of $R^2$, $R^3$, $R^4$, $R^5$, $R^6$, and $R^7$ are optionally combined with one another, and

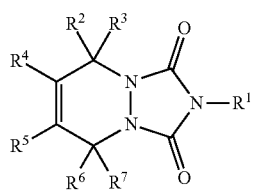

(4)

in which in the formula (4), $R^1$ is as defined in the formula (1); and $R^2$, $R^3$, $R^4$, $R^5$, $R^6$, and $R^7$ are as defined in the formula (3).

In the method for analyzing a diene compound according to the aspect of the present invention, the triazolinedione adduct is heated before mixing the triazolinedione adduct with the diene compound, to produce the triazolinedione compound. This allows for the generation of the triazolinedione compound required for the reaction, while decomposition of the triazolinedione compound generated is suppressed.

Moreover, since thermal deterioration of the diene compound to be analyzed can be suppressed, a derivatization reaction of the diene compound can be performed smoothly, and analysis of a trace amount of diene compound can be made.

Therefore, the method for analyzing a diene compound according to the aspect of the present invention enables the triazolinedione adduct as an analysis reagent to be applied to the quantitative determination of diene compounds with sufficient sensitivity and accuracy.

DETAILED DESCRIPTION OF THE INVENTION

Hereinafter, embodiments of the present invention will be described. It should be noted that the embodiments described below are not intended to limit the present invention.

<Analysis Method of Diene Compound>

The method for analyzing a diene compound according to the present disclosure performs analysis of a trace amount of diene compound which is a substance to be analyzed, using a triazolinedione adduct as an analysis reagent, and includes a triazolinedione adduct heating step, an ene compound formation step, and an ene compound analysis step. The method for analyzing a diene compound according to the present disclosure is required to include these steps as essential steps, and may optionally include other step(s).

The method for analyzing a diene compound according to the present disclosure is best characterized in that the method includes the triazolinedione adduct heating step, and specifically, that the triazolinedione adduct is heated in the absence of the diene compound being a substance to be analyzed, to generate the triazolinedione compound. Hereinafter, the method for analyzing a diene compound according to the present disclosure will be described.

[Triazolinedione Adduct Heating Step]

The triazolinedione adduct heating step is a characteristic step of the method for analyzing a diene compound according to the present disclosure, and is a step of heating a triazolinedione adduct represented by the following formula (1) to produce a triazolinedione compound represented by the following formula (2).

[Triazolinedione Adduct]

The triazolinedione adduct for use as an analysis reagent in the method for analyzing a diene compound according to the present disclosure is represented by the following formula (1).

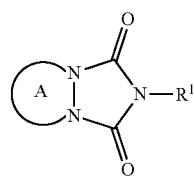

(1)

In the formula (1), $R^1$ represents an organic group; and A represents a fused ring having three or more rings including at least one aromatic ring.

Preferably, $R^1$ in the above formula (1) represents a group selected from the group consisting of a substituted or unsubstituted phenyl group, a substituted or unsubstituted naphthyl group, a substituted or unsubstituted anthracenyl group, a substituted or unsubstituted nitrogen-containing heterocyclic group, and a substituted or unsubstituted alkyl group.

More preferably, $R^1$ in the above formula (1) represents a substituted or unsubstituted phenyl group.

Even more preferably, $R^1$ in the above formula (1) represents a phenyl group which may have a substituent selected from the group consisting of a disubstituted amino group, a disubstituted aminoalkyl group, a nitro group, an azide group, an alkoxy group, a halogen group, an alkylthio group, a sulfonyl group, a phosphoric acid group, a carboxy group, an ester group, a nitrile group, an amide group, a ferrocenyl group, and a substituted quinoxalinyl group, in which the two substituents included in the disubstituted amino group or the disubstituted aminoalkyl group are identical to or different from each other and are each selected from the group consisting of an alkyl group, an aralkyl group, and an aryl group, and in which the alkyl group, the aralkyl group and the aryl group optionally contain an oxygen atom or a nitrogen atom.

Still more preferably, $R^1$ in the above formula (1) represents a phenyl group having an alkylamino group or an alkylaminoalkyl group.

Particularly preferably, $R^1$ in the above formula (1) represents a phenyl group having a dialkylamino group or a dialkylaminoalkyl group, and most preferably, represents a phenyl group that has a group selected from the group consisting of a 4-dimethylaminophenyl group, a 4-diethylaminophenyl group, and a 4-dimethylaminomethylphenyl group.

Examples of the triazolinedione adduct represented by the above formula (1) include a triazolinedione adduct represented by the following formula (5).

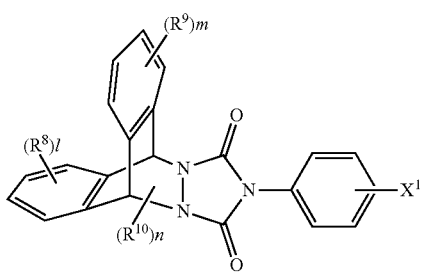

(5)

In the formula (5), $X^1$ represents an organic group; $R^8$, $R^9$ and $R^{10}$ each independently represent a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group; l and m are each independently an integer of 0 to 4; and n is an integer of 0 to 2.

Preferably, $X^1$ in the above formula (5) represents a group selected from the group consisting of a disubstituted amino group, a disubstituted aminoalkyl group, a nitro group, an azide group, an alkoxy group, a halogen group, an alkylthio group, a sulfonyl group, a phosphoric acid group, a carboxy group, an ester group, a nitrile group, an amide group, a ferrocenyl group, and a substituted quinoxalinyl group, in which the two substituents included in the disubstituted amino group or the disubstituted aminoalkyl group are identical to or different from each other and are each selected from the group consisting of an alkyl group, an aralkyl group, and an aryl group, and in which the alkyl group, the aralkyl group and the aryl group optionally contain an oxygen atom or a nitrogen atom.

More preferably, $X^1$ in the above formula (5) represents an alkylamino group or an alkylaminoalkyl group.

Particularly preferably, $X^1$ in the above formula (5) represents a dialkylamino group or a dialkylaminoalkyl group, and most preferably, a dimethylamino group or a diethylamino group.

With regard to $R^8$, $R^9$, and $R^{10}$ mentioned above, examples of the substituent which may be included in the substituent selected from the group consisting of an alkyl group, an aralkyl group, an alkenyl group, a phenyl group, an acyl group, an amino group, and a heterocyclic group include: alkyl groups such as a methyl group, an ethyl group, a propyl group, a butyl group, an isobutyl group, a t-butyl group, a chloromethyl group, a 2-chloroethyl group, a 3-chloropropyl group, a 2-chloropropyl group, a 1-chloropropyl group, a bromomethyl group, a 2-bromoethyl group, a 3-bromopropyl group, a 2-bromopropyl group, and a 1-bromopropyl group; aralkyl groups such as a benzyl group, a phenethyl group, a 3-phenylpropyl group, a 4-methylbenzyl group, and a 4-methylphenethyl group; alkenyl groups such as a vinyl group, an allyl group, a propenyl group, a cyclopropenyl group, a 2-chlorovinyl group, a 3-chloroallyl group, a cinnamyl group, and a styryl group; phenyl groups such as a phenyl group, a tolyl group, a xylyl group, and a trityl group; acyl groups such as a formyl group, an acetyl group, a propionyl group, a benzoyl group, an acryloyl group, and a methacryloyl group; halogen groups such as a chloro group, a bromo group, a fluoro group, and an iodo group; amino groups such as an amino group, a methylamino group, a dimethylamino group, an ethylamino group, and a diethylamino group; a nitro group; heterocyclic groups such as a quinolyl group, a pyridyl group, a pyrrolidyl group, a pyrrolyl group, a furyl group, a thienyl group, and a lutidyl group; and the like.

Examples of the triazolinedione adduct represented by the above formula (5) include those represented by the following formulae (5-1) and (5-2).

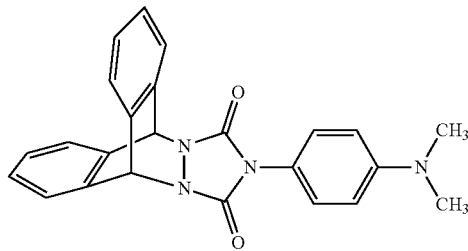

(5-1)

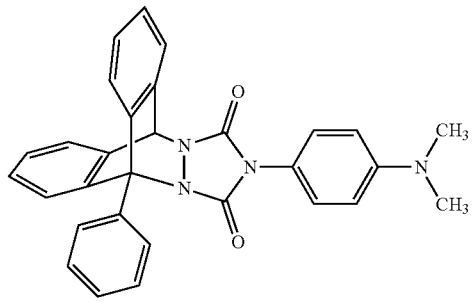

(5-2)

In addition, examples of the triazolinedione adduct represented by the above formula (1) include a triazolinedione adduct represented by the following formula (6).

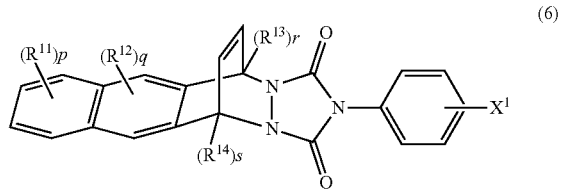

(6)

In the formula (6), $X^1$ represents an organic group; $R^{11}$, $R^{12}$, $R^{13}$, and $R^{14}$ each independently represent a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group; p is an integer of 0 to 4; q is an integer of 0 to 2; and r and s are each 0 or 1.

Preferably, $X^1$ in the above formula (6) represents a group selected from the group consisting of a disubstituted amino group, a disubstituted aminoalkyl group, a nitro group, an azide group, an alkoxy group, a halogen group, an alkylthio group, a sulfonyl group, a phosphoric acid group, a carboxy group, an ester group, a nitrile group, an amide group, a ferrocenyl group, and a substituted quinoxalinyl group, in which the two substituents included in the disubstituted amino group or the disubstituted aminoalkyl group are identical to or different from each other and are each selected from the group consisting of an alkyl group, an aralkyl group, and an aryl group, and in which the alkyl group, the aralkyl group and the aryl group optionally contain an oxygen atom or a nitrogen atom.

More preferably, $X^1$ in the above formula (6) represents an alkylamino group or an alkylaminoalkyl group.

Particularly preferably, $X^1$ in the above formula (6) represents a dialkylamino group or a dialkylaminoalkyl group, and most preferably, a dimethylamino group or a diethylamino group.

With regard to $R^{11}$, $R^{12}$, $R^{13}$, and $R^{14}$ mentioned above, examples of the substituent which may be included in the substituent selected from the group consisting of an alkyl group, an aralkyl group, an alkenyl group, a phenyl group, an acyl group, an amino group, and a heterocyclic group include: alkyl groups such as a methyl group, an ethyl group, a propyl group, a butyl group, an isobutyl group, a t-butyl group, a chloromethyl group, a 2-chloroethyl group, a 3-chloropropyl group, a 2-chloropropyl group, a 1-chloropropyl group, a bromomethyl group, a 2-bromoethyl group, a 3-bromopropyl group, a 2-bromopropyl group, and a 1-bromopropyl group; aralkyl groups such as a benzyl group, a phenethyl group, a 3-phenylpropyl group, a 4-methylbenzyl group, and a 4-methylphenethyl group; alkenyl groups such as a vinyl group, an allyl group, a propenyl group, a cyclopropenyl group, a 2-chlorovinyl group, a 3-chloroallyl group, a cinnamyl group, and a styryl group; phenyl groups such as a phenyl group, a tolyl group, a xylyl group, and a trityl group; acyl groups such as a formyl group, an acetyl group, a propionyl group, a benzoyl group, an acryloyl group, and a methacryloyl group; halogen groups such as a chloro group, a bromo group, a fluoro group, and an iodo group; amino groups such as an amino group, a methylamino group, a dimethylamino group, an ethylamino group, and a diethylamino group; a nitro group; heterocyclic groups such as a quinolyl group, a pyridyl group, a pyrrolidyl group, a pyrrolyl group, a furyl group, a thienyl group, and a lutidyl group; and the like.

[Production Method of Triazolinedione Adduct]

In the method for analyzing a diene compound according to an embodiment of the present invention, triazolinedione adducts produced using a known method may be employed without limitation as the triazolinedione adduct represented by the above formula (1), which is used as an analysis reagent. For example, a triazolinedione adduct which can be obtained by reacting a triazolidinedione compound represented by the following formula (7) with a fused ring compound including at least two aromatic rings in the presence of an oxidizing agent can be employed. In the production of the triazolinedione adduct, an additive such as a desiccant may be added as long as the additive does not interfere with the reaction.

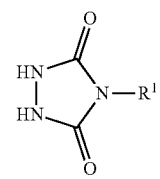

(7)

In the formula (7), $R^1$ is as defined in the above formula (1).

(Triazolidinedione Compound)

The compound represented by the above formula (7), which is an ingredient material of the triazolinedione adduct, is a triazolidinedione compound that includes a urazole group, i.e., a triazolidinedione compound which includes a 1,2,4-triazolidine-3,5-dione group.

Preferably, $R^1$ in the above formula (7) represents a group selected from the group consisting of a substituted or unsubstituted phenyl group, a substituted or unsubstituted naphthyl group, a substituted or unsubstituted anthracenyl group, a substituted or unsubstituted nitrogen-containing heterocyclic group, and a substituted or unsubstituted alkyl group.

More preferably, $R^1$ in the above formula (7) represents a substituted or unsubstituted phenyl group.

Even more preferably, $R^1$ in the above formula (7) represents a phenyl group which may have a substituent selected from the group consisting of a disubstituted amino group, a disubstituted aminoalkyl group, a nitro group, an azide group, an alkoxy group, a halogen group, an alkylthio group, a sulfonyl group, a phosphoric acid group, a carboxy group, an ester group, a nitrile group, an amide group, a ferrocenyl group, and a substituted quinoxalinyl group, in which the two substituents included in the disubstituted amino group or the disubstituted aminoalkyl group are identical to or different from each other and are each selected from the group consisting of an alkyl group, an aralkyl group, and an aryl group, and in which the alkyl group, the aralkyl group and the aryl group optionally contain an oxygen atom or a nitrogen atom.

Still more preferably, $R^1$ in the above formula (7) represents a phenyl group having an alkylamino group or an alkylaminoalkyl group.

Particularly preferably, $R^1$ in the above formula (7) represents a phenyl group having a dialkylamino group or a dialkylaminoalkyl group, and most preferably, represents a phenyl group that has a group selected from the group consisting of a 4-diethylaminophenyl group, a 4-dimethylaminophenyl group, and a 4-dimethylaminomethylphenyl group.

Therefore, the most preferable compound represented by the above formula (7) is 4-(4'-diethylaminophenyl)-1,2,4-triazolidine-3,5-dione, 4-(4'-dimethylaminophenyl)-1,2,4-triazolidine-3,5-dione (DMU), or 4-(4'-dimethylaminomethylphenyl)-1,2,4-triazolidine-3,5-dione.

(Fused Ring Compound Including at Least Two Aromatic Rings)

Examples of the fused ring compound including at least two aromatic rings, which is reacted with the triazolidinedione compound represented by the above formula (7) for the production of the triazolinedione adduct, include compounds having a backbone represented by any one of the following formulae (7-1) to (7-12). A part of hydrogen atoms included in these fused ring compounds having such a backbone may be substituted with a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group. Examples of the substituent which may be included in the substituent selected from the group consisting of an alkyl group, an aralkyl group, an alkenyl group, a phenyl group, an acyl group, an amino group, and a heterocyclic group include: alkyl groups such as a methyl group, an ethyl group, a propyl group, a butyl group, an isobutyl group, a t-butyl group, a chloromethyl group, a 2-chloroethyl group, a 3-chloropropyl group, a 2-chloropropyl group, a 1-chloropropyl group, a bromomethyl group, a 2-bromoethyl group, a 3-bromopropyl group, a 2-bromopropyl group, and 1-bromopropyl group; aralkyl groups such as a benzyl group, a phenethyl group, a 3-phenylpropyl group, a 4-methylbenzyl group, and a 4-methylphenethyl group; alkenyl groups such as a vinyl group, an allyl group, a propenyl group, a cyclopropenyl group, a 2-chlorovinyl group, a 3-chloroallyl group, a cinnamyl group, and a styryl group; phenyl groups such as a phenyl group, a tolyl group, a xylyl group, and a trityl group; acyl groups such as a formyl group, an acetyl group, a propionyl group, a benzoyl group, an acryloyl group, and a methacryloyl group; halogen groups such as a chloro group, a bromo group, a fluoro group, and an iodo group; amino groups such as an amino group, a methylamino group, a dimethylamino group, an ethylamino group, and a diethylamino group; a nitro group; heterocyclic groups such as a quinolyl group, a pyridyl group, a pyrrolidyl group, a pyrrolyl group, a furyl group, a thienyl group, and a lutidyl group; and the like. Moreover, at least one selected from a cyclic alkyl group having 1 to 20 carbon atoms, a phenyl group, and a heterocyclic group may be fused with any of these fused ring compounds having such a backbone.

The fused ring compound including at least two aromatic rings, which is subjected to the reaction with the triazolidinedione compound represented by the above formula (7), is preferably a compound having a backbone represented by the following formula (7-5) in light of the ease with which the reverse reaction (retro-Diels-Alder reaction) takes place in the triazolinedione adduct heating step.

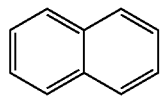
(7-1)

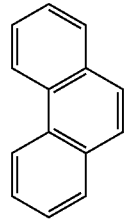
(7-2)

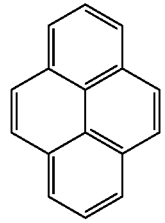
(7-3)

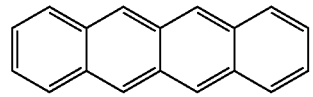
(7-4)

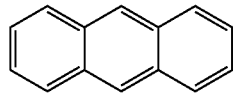
(7-5)

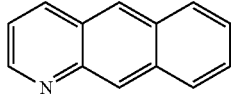
(7-6)

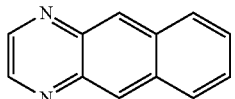
(7-7)

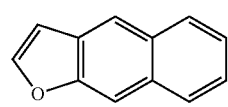
(7-8)

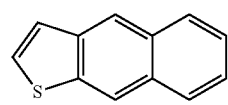
(7-9)

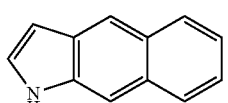
(7-10)

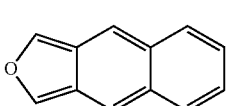
(7-11)

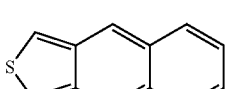
(7-12)

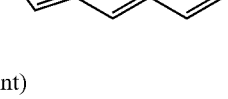

(Oxidizing Agent)

With regard to the production of the triazolinedione adduct, the oxidizing agent in the presence of which the reaction of the triazolidinedione compound represented by the above formula (7) with the aforementioned fused ring compound including at least two aromatic rings is carried out is not particularly limited as long as the triazolinedione adduct represented by the above formula (1) can be formed. However, the oxidizing agent is preferably a hypervalent iodine compound. The hypervalent iodine compound allows for smooth transformation from the triazolidinedione compound to the triazolinedione, and enables the subsequent reaction of the triazolinedione with the fused ring compound including at least two aromatic rings to proceed without any delay.

(Additive)

In the production of the triazolinedione adduct, it is also possible to add an additive such as a desiccant as long as the additive does not interfere with the reaction of the triazolidinedione compound represented by the above formula (7) with the fused ring compound including at least two aromatic rings. Examples of the additive include magnesium sulfate, sodium sulfate, potassium carbonate, calcium chloride, silica gel, molecular sieves, and the like.

[Reaction Conditions]

(Reaction Solvent)

In the production of the triazolinedione adduct, the reaction solvent for use in the reaction of the triazolidinedione compound represented by the above formula (7) with the fused ring compound including at least two aromatic rings in the presence of the oxidizing agent is preferably at least one selected from the group consisting of esters, halogen-containing hydrocarbons, aromatic hydrocarbons, ketones, amides, alkylnitriles, dialkyl ethers, and ureas. Meanwhile, the diene compound to be subjected to the reaction per se may be used as the solvent.

The amount of the solvent used in the reaction is preferably 5 to 1000 volumes with respect to 1 part by mass of the triazolidinedione compound.

(Reaction Temperature)

The temperature for the reaction of the triazolidinedione compound represented by the above formula (7) with the fused ring compound including at least two aromatic rings in the presence of the oxidizing agent is preferably in the range of −10° C. to 60° C., and more preferably in the range of 0° C. to 40° C.

(Reaction Time Period)

The time period for the reaction of the triazolidinedione compound represented by the above formula (7) with the fused ring compound including at least two aromatic rings in the presence of the oxidizing agent is preferably 10 minutes to 48 hours, and more preferably in the range of 1 to 10 hours.

(Feed Amount)

The amount of the fused ring compound including at least two aromatic rings is preferably in the range of 1.0 to 10000 equivalents with respect to 1 equivalent of the triazolidinedione compound.

The amount of the oxidizing agent used is preferably 1 to 10 mol equivalents, and more preferably 1 to 5 mol equivalents with respect to the triazolidinedione compound. The range of 1 to 5 mol equivalents makes it easy to remove the oxidizing agent and decomposition products thereof which remain after the reaction.

When the additive is used, the amount of the additive is not particularly limited as long as the additive does not interfere with the reaction. For example, when the additive is magnesium sulfate, the amount of the additive is preferably in the range of 1 to 50 mol equivalents.

(Solidification and Purification)

The resultant triazolinedione adduct represented by the above formula (1) may be crystallized and recovered as a solid.

After the crystallization, purification may be further performed in pursuit of higher purity. The method for the purification is exemplified by recrystallization, column purification, and the like. The resultant solid matter of the triazolinedione adduct can be isolated through solid-liquid separation by solvent distillation, filtration, centrifugation or the like, followed by drying through air-drying, fan drying, vacuum drying, or the like.

[Triazolinedione Compound]

In the triazolinedione adduct heating step of the present disclosure, the triazolinedione adduct represented by the above formula (1) is heated, to produce the triazolinedione compound represented by the following formula (2).

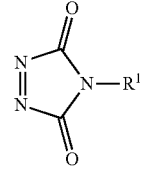

In the formula (2), $R^1$ is as defined in the above formula (1).

More specifically, in the triazolinedione adduct heating step, the triazolinedione adduct represented by the above formula (1) is heated to cause the reverse reaction (retro-Diels-Alder reaction) to the triazolinedione compound represented by the above formula (2) and the fused ring compound including at least two aromatic rings. That is, the triazolinedione adduct heating step of the present disclosure produces the triazolinedione compound from the triazolinedione adduct through the reverse reaction.

Therefore, the triazolinedione compound represented by the above formula (2) produced in the triazolinedione adduct heating step is generated from the triazolinedione adduct represented by the above formula (1). Thus, the triazolinedione compound represented by the above formula (2) is exemplified by 4-phenyl-1,2,4-triazoline-3,5-dione (PTAD), 4-methyl-1,2,4-triazoline-3,5-dione (MTAD), 4-[2-(6,7-dimethoxy-4-methyl-3-oxo-3,4-dihydroquinoxalinyl)ethyl]-1, 2,4-triazoline-3,5-dione (DMEQTAD), 4-(4-nitrophenyl)-1, 2,4-triazoline-3,5-dione (NPTAD), 4-ferrocenylmethyl-1,2, 4-triazoline-3,5-dione (FMTAD), 4-(6-quinolyl)-1,2,4-triazoline-3,5-dione (QTAD), 4-(4'-diethylaminophenyl)-1, 2,4-triazoline-3,5-dione (DEAPTAD), 4-(4'-dimethylaminophenyl)-1,2,4-triazoline-3,5-dione (DAPTAD), and 4-(4'-dimethylaminomethylphenyl)-1,2,4-triazoline-3,5-dione, and the like. These triazolinediones can serve as the Cookson-type derivatization reagent.

Preferably, $R^1$ in the above formula (2) represents a group selected from the group consisting of a substituted or unsubstituted phenyl group, a substituted or unsubstituted naphthyl group, a substituted or unsubstituted anthracenyl group, a substituted or unsubstituted nitrogen-containing heterocyclic group, and a substituted or unsubstituted alkyl group.

More preferably, $R^1$ in the above formula (2) represents a substituted or unsubstituted phenyl group.

Even more preferably, $R^1$ in the above formula (2) represents a phenyl group which may have a substituent selected from the group consisting of a disubstituted amino group, a disubstituted aminoalkyl group, a nitro group, an azide group, an alkoxy group, a halogen group, an alkylthio group, a sulfonyl group, a phosphoric acid group, a carboxy group, an ester group, a nitrile group, an amide group, a ferrocenyl group, and a substituted quinoxalinyl group, in which the two substituents included in the disubstituted amino group or the disubstituted aminoalkyl group are identical to or different from each other and are each selected from the group consisting of an alkyl group, an aralkyl group, and an aryl group, and in which the alkyl group, the aralkyl group and the aryl group optionally contain an oxygen atom or a nitrogen atom.

Still more preferably, $R^1$ in the above formula (2) represents a phenyl group having an alkylamino group or an alkylaminoalkyl group.

Particularly preferably, $R^1$ in the above formula (2) represents a phenyl group having a dialkylamino group or a dialkylaminoalkyl group, and most preferably, represents a phenyl group that has a group selected from the group consisting of a 4-diethylaminophenyl group, a 4-dimethylaminophenyl group, and a 4-dimethylaminomethylphenyl group.

Therefore, the triazolinedione compound represented by the above formula (2) is particularly preferably 4-phenyl-1,2,4-triazoline-3,5-dione, 4-(4'-diethylaminophenyl)-1,2,4-triazoline-3,5-dione, 4-(4'-dimethylaminophenyl)-1,2,4-triazoline-3,5-dione (DAPTAD), or 4-(4'-dimethylaminomethylphenyl)-1,2,4-triazoline-3,5-dione.

[Conditions for Heating]
(Reaction Solvent)

As the solvent for use in causing the reverse reaction (retro-Diels-Alder reaction) in the triazolinedione adduct heating step, solvents commonly used for such a reaction may be used without particular limitation. An aprotic solvent which stabilizes the resulting triazolinedione compound to a greater extent is preferable, and specifically, ethyl acetate, acetonitrile, and dioxane are preferable. Among these, ethyl acetate is more preferable in light of favorable handleability.

(Reaction Temperature)

The temperature for causing the reverse reaction (retro-Diels-Alder reaction) in the triazolinedione adduct heating step is preferably in the range of 50° C. to 100° C. The temperature is more preferably in the range of 70° C. to 100° C. in light of the rate of reaction of the retro-Diels-Alder reaction. Even more preferably, the temperature is in the range of 70° C. to 80° C. in light of a sufficient rate of the retro-Diels-Alder reaction, as well as stability of the triazolinedione compound generated and boiling points of general solvents. For example, when the solvent is ethyl acetate, a temperature of 77° C. to 80° C. is suitable.

(Reaction Time Period)

The reaction time period for causing the reverse reaction (retro-Diels-Alder reaction) in the triazolinedione adduct heating step is preferably 10 minutes to 5 hours. A longer reaction time period may cause decomposition of the triazolinedione compound. On the other hand, an excessively short reaction time period may fail to generate a sufficient amount of the triazolinedione compound for the reaction with the diene compound in the next step, i.e., the ene compound formation step. More preferably, the reaction time period is 5 to 30 minutes.

[Ene Compound Formation Step]

The ene compound formation step is a step of reacting the triazolinedione compound produced in the triazolinedione adduct heating step with a diene compound represented by the following formula (3), to obtain an ene compound represented by the following formula (4).

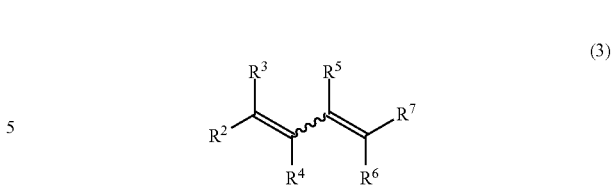

(3)

In the formula (3), $R^2$, $R^3$, $R^4$, $R^5$, $R^6$, and $R^7$ each independently represent a group selected from the group consisting of a hydrogen atom, an alkyl group having 1 to 100 carbon atoms, an aralkyl group, a phenyl group, and a heterocyclic group, in which the alkyl group, the aralkyl group, the phenyl group and the heterocyclic group optionally contain an atom selected from the group consisting of an oxygen atom, a nitrogen atom, a sulfur atom, and a phosphorus atom, and in which at least two of $R^2$, $R^3$, $R^4$, $R^5$, $R^6$, and $R^7$ are optionally combined with one another.

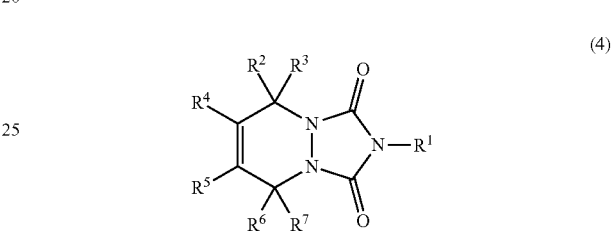

(4)

In the formula (4), $R^1$ is as defined in the formula (1); and $R^2$, $R^3$, $R^4$, $R^5$, $R^6$, and $R^7$ are as defined in the above formula (3).

[Diene Compound]

The diene compound represented by the above formula (3), which is subjected to the reaction with the triazolinedione compound produced thus, is a substance to be analyzed in the method for analyzing a diene compound according to the present disclosure.

The diene compound represented by the above formula (3) is preferably a compound selected from the group consisting of natural products of higher or lower molecular weight, bioactive compounds including pharmaceuticals, functional materials, and intermediates thereof, in light of its higher degree of utility.

Thus, the diene compound represented by the above formula (3), which is to be analyzed, is preferably an anthracene derivative, a quinoline derivative, a vitamin, an amino acid, a steroid, or the like, in which $R^2$, $R^3$, $R^4$, $R^5$, $R^6$, and $R^7$ in the above formula (3) each have the aforementioned substituent.

Among these, the diene compound represented by the above formula (3), which is to be analyzed, is preferably a vitamin, since the triazolinedione adduct represented by the above formula (1) serves as the Cookson-type derivatization reagent. Specifically, the diene compound represented by the above formula (3) is preferably at least one selected from the group consisting of vitamin D2, vitamin D3, vitamin A, 25-hydroxyvitamin D3, 3-epi-25-hydroxyvitamin D3, and 24R,25-dihydroxyvitamin D3.

[Ene Compound]

The ene compound represented by the above formula (4), which is obtained by reacting the triazolinedione compound and the diene compound represented by the above formula (3), is a substance to be analyzed in the ene compound analysis step, as described later.

The ene compound represented by the above formula (4) is derived from the diene compound represented by the above formula (3). Thus, $R^2$, $R^3$, $R^4$, $R^5$, $R^6$, and $R^7$ in the ene compound represented by the above formula (4) each have the same structure as those in the diene compound represented by the above formula (3). In other words, $R^2$, $R^3$, $R^4$, $R^5$, $R^6$, and $R^7$ in the ene compound represented by the above formula (4) are preferably an anthracene derivative, a quinoline derivative, a vitamin, an amino acid, a steroid, or the like, which has the aforementioned substituent.

[Reaction Conditions]
(Reaction Solvent)

The solvent for use in reacting the triazolinedione compound represented by the above formula (2) with the diene compound represented by the above formula (3) is not particularly limited as long as a solvent commonly used for such a reaction is employed. However, the solvent is an aprotic solvent in light of solution stability of the triazolinedione compound, and is preferably a hydrocarbon solvent. The hydrocarbon solvent is exemplified by ethyl acetate, acetonitrile, dioxane, toluene, hexane, and the like.

In the method for analyzing a diene compound according to the present disclosure, the ene compound formation step for performing the reaction with the diene compound is carried out subsequently to the triazolinedione adduct heating step for producing the triazolinedione compound. Therefore, a solvent employed in the ene compound formation step is preferably the same as the solvent employed in the triazolinedione adduct heating step.

The amount of the solvent used in the reaction is preferably 5 to 1000 volumes with respect to 1 part by mass of the triazolinedione compound.

(Reaction Temperature)

The temperature for reacting the triazolinedione compound represented by the above formula (2) with the diene compound represented by the above formula (3) is preferably in the range of −20° C. to 200° C., and more preferably in the range of 0 to 50° C. in light of stability of the diene compound and the triazolinedione compound.

(Reaction Time Period)

Moreover, the time period for reacting the triazolinedione compound represented by the above formula (2) with the diene compound represented by the above formula (3) is preferably 1 minute to 12 hours, and more preferably in the range of 15 minutes to 1 hour.

(Feed Amount)

In the reaction of the triazolinedione compound represented by the above formula (2) with the diene compound represented by the above formula (3), the amount of the triazolinedione compound represented by the above formula (2) used is not particularly limited as long as the amount of the triazolinedione compound represented by the above formula (2) is in excess over the amount of the diene compound represented by the above formula (3). For example, in the case where the diene compound represented by the above formula (3) is a vitamin, the amount of the triazolinedione compound is preferably in the range of 1 to 1,000,000 equivalents, more preferably in the range of 10 to 1,000,000 equivalents, and most preferably in the range of 1,000 to 1,000,000 equivalents with respect to 1 equivalent of the diene compound.

[Ene Compound Analysis Step]

The ene compound analysis step is a step of analyzing the ene compound obtained in the ene compound formation step to quantitatively determine the diene compound subjected to the reaction in the ene compound formation step.

The ene compound represented by the above formula (4), which is formed in the ene compound formation step, tends to exhibit strong ultraviolet-visible absorption and is easily ionized due to its structure. Therefore, the sensitivity of the ene compound is increased for a variety of analysis methods.

[Analysis Method]

Although the method for analyzing the ene compound represented by the above formula (4) is not particularly limited, a method employing mass spectrometry or high performance liquid chromatography is preferable in light of high sensitivity, accuracy, and ease of handling. Alternatively, combinations of the two techniques, i.e., high performance liquid chromatography-mass spectrometry (LC-MS), and high performance liquid chromatography-tandem mass spectrometry (LC-MS/MS), may be employed.

(High Performance Liquid Chromatography)

The detector in the high performance liquid chromatography is not particularly limited as long as a substance to be analyzed can be measured. The detector is exemplified by an ultraviolet-visible spectrometric detector, a photodiode array detector, a fluorescent detector, an RI detector, an evaporative light scattering detector, and the like.

The column used in the high performance liquid chromatography is not particularly limited as long as a substance to be analyzed can be measured. However, a column containing chemically-bonded porous spherical silica gels surface-modified by an octadecylsilyl group is preferable in light of higher degree of versatility.

Analytical conditions for the high performance liquid chromatography are not particularly limited as long as the conditions permit measurement of a substance to be analyzed.

Solvents commonly used may be employed as an eluent. The eluent is exemplified by methanol, acetonitrile, hexane, chloroform, ethyl acetate, tetrahydrofuran, distilled water, an aqueous formic acid solution, an aqueous carbonic acid solution, and an aqueous phosphoric acid solution. One type or two or more types of solvents may be used in a combination thereof, and use of a combination of distilled water or an aqueous solution and an organic solvent is preferable in light of ease in adjusting a measurement time period of a substance to be analyzed. Among these, the following combinations are suitable in light of ease in combination with the mass spectrometry: distilled water/acetonitrile, distilled water/methanol, aqueous formic acid solution/acetonitrile, and aqueous formic acid solution/methanol.

(Mass Spectrometry)

The mass spectrometry is not particularly limited as long as a commercially available mass spectrometry is used.

As an ion source of the mass spectrometry, for example, electron ionization (EI) method, chemical ionization (CI) method, field desorption (FD) method, fast atom bombardment (FAB) method, matrix-assisted laser desorption ionization (MALDI) method, electrospray ionization (ESI) method, atmospheric pressure chemical ionization (APCI) method, direct analysis in real time (DART) method, ion attachment method, inductively coupled plasma (ICP) method or the like may be employed. Among these, electrospray ionization (ESI) method, and atmospheric pressure chemical ionization (APCI) method are suitable in light of ease in combination with the high performance liquid chromatography.

The mass separation unit of mass spectrometry is exemplified by a mass separation unit of a magnetic deflection type, a quadrupole type, an ion trap type, a time-of-flight type, a Fourier transform ion cyclotron resonance type, a tandem type, and the like.

19

<Production Method of Ene Compound>

The method for producing an ene compound according to the present disclosure uses a triazolinedione adduct as an analysis reagent to convert a trace amount of diene compound, i.e., a substance to be analyzed, to an ene compound which can be analyzed more easily, and includes a triazolinedione adduct heating step, and an ene compound formation step. The method for producing an ene compound according to the present invention is required to include these steps as essential steps, and may optionally include other step(s).

The method for producing an ene compound according to the present disclosure is best characterized in that the method includes the triazolinedione adduct heating step, and specifically, that the triazolinedione adduct is heated in the absence of the diene compound being a substance to be analyzed, to produce the triazolinedione compound.

It is to be noted that the triazolinedione adduct heating step and the ene compound formation step in the method for producing an ene compound according to the present disclosure are respectively identical to the triazolinedione adduct heating step and the ene compound formation step in the method for analyzing a diene compound according to the present invention as described above.

EXAMPLES

Next, Examples of the present invention will be described, but the present invention is not limited to these Examples.

Production Example 1

[Synthesis of 9-Phenylanthracene Adduct (DAP-PA)]

A mixture of 4-(4'-dimethylaminophenyl)-1,2,4-triazolidine-3,5-dione (0.429 g, 1.95 mmol), iodosylbenzene (0.429 g, 1.95 mmol), 9-phenylanthracene (0.496 g, 1.95 mmol) and magnesium sulfate (0.429 g, 3.56 mmol) in 21.5 mL of ethyl acetate was stirred at room temperature for 24 hours.

The mixture was filtered, then 300 mL of hexane was added to the filtrate. The mixture was stirred for 2 hours in an ice-water bath. The precipitate was collected by filtration and dried under reduced pressure to give 5,10-dihydro-2-(4-dimethylaminophenyl)-5-phenyl-5,10[1',2']-benzeno-1H-[1,2,4]triazolo[1,2-b]phthalazine-1,3(2H)-dione (DAP-PA) (0.54 g, 58.6%).

[Reaction Scheme]

The reaction scheme executed in Production Example 1 is shown below.

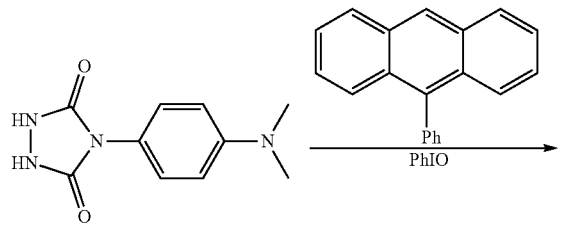

20

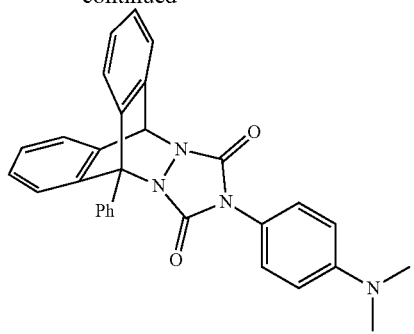

DAP-PA

[Evaluation of Physical Properties]

Various analyses were carried out on the resultant DAP-PA. The results are shown below.

Mp: >200° C.

IR (KBr): 1774, 1714 $cm^{-1}$ $^1$H-NMR (CDCl$_3$): δ 6.25-8.10 (m, 17H), 2.80 (s, 6H)

Production Example 2

[Synthesis of 9,10-Diphenylanthracene Adduct (DAP-DPA)]

A mixture of 4-(4'-dimethylaminophenyl)-1,2,4-triazolidine-3,5-dione (0.50 g, 2.27 mmol), iodosylbenzene (0.50 g, 2.27 mmol), 9,10-diphenylanthracene (0.75 g, 2.27 mmol) and magnesium sulfate (0.50 g, 4.15 mmol) in 25 mL of toluene was stirred at room temperature for 24 hours.

The mixture was filtered, then 300 mL of hexane was added to the filtrate. The mixture was stirred for 2 hours in an ice-water bath. The precipitate was collected by filtration and dried under reduced pressure to give 12-dihydro-2-(4-dimethylaminophenyl)-6,11-diphenyl-5,12-etheno-1H-benzo[g][1,2,4]triazolo[1,2-b]phthalazine-1,3(2H)-dione (DAP-DPA) (43 mg, 3.4%).

[Reaction Scheme]

The reaction scheme executed in Production Example 2 is shown below.

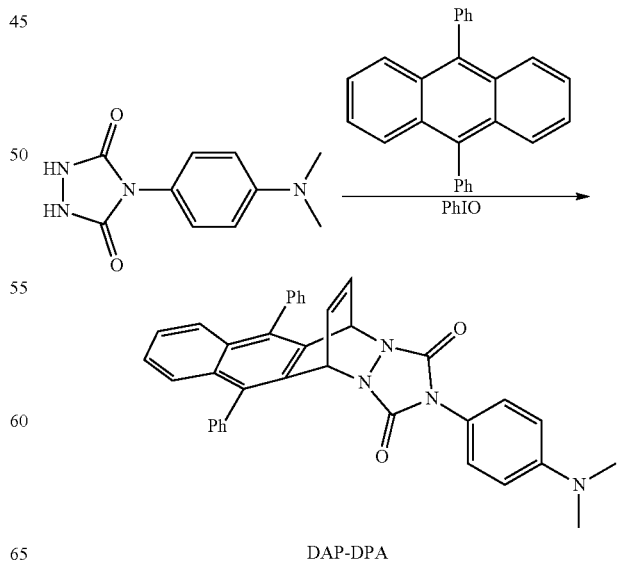

DAP-DPA

[Evaluation of Physical Properties]

Various analyses were carried out on the resultant DAP-DPA. The results are shown below.

Mp: >200° C.

IR (KBr): 1764, 1705 cm$^{-1}$ $^1$H-NMR (DMSO-d$_6$): δ 7.30-8.00 (m, 16H), 6.70-7.30 (m, 4H), 5.50-5.80 (m, 2H), 2.90 (s, 6H)

Production Example 3

[Synthesis of 9-Methylanthracene Adduct (DAP-MA)]

A mixture of 4-(4'-dimethylaminophenyl)-1,2,4-triazolidine-3,5-dione (99.1 mg, 0.45 mmol), iodosylbenzene (99.0 g, 0.45 mmol), 9-methylanthracene (86.5 mg, 0.45 mmol) and magnesium sulfate (99.0 mg, 0.82 mmol) in 5.0 mL of ethyl acetate was stirred at room temperature for 24 hours.

The mixture was filtered, then 100 mL of hexane was added to the filtrate. The mixture was stirred for 2 hours in an ice-water bath. The precipitate was collected by filtration and dried under reduced pressure to give 5,10-dihydro-2-(4-dimethylaminophenyl)-5-methyl-5,10[1',2']-benzeno-1H-[1,2,4]triazolo[1,2-b]phthalazine-1,3(2H)-dione (DAP-MA) (95 mg, 51.4%).

[Reaction Scheme]

The reaction scheme executed in Production Example 3 is shown below.

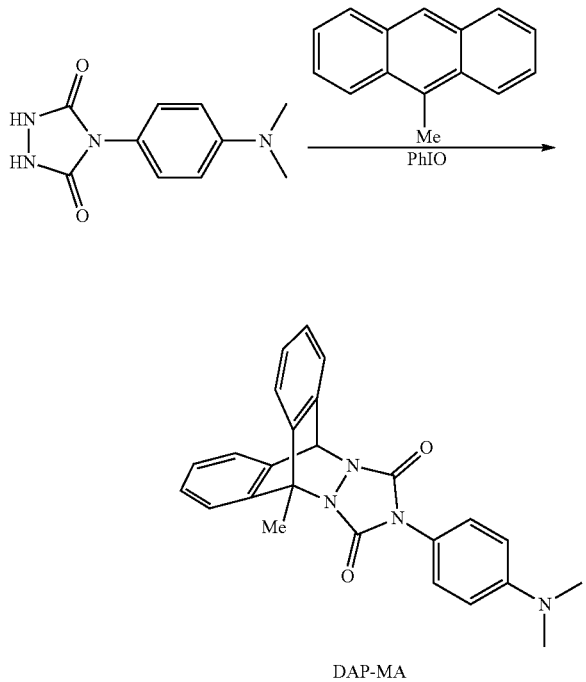

DAP-MA

[Evaluation of Physical Properties]

Various analyses were carried out on the resultant DAP-MA. The results are shown below.

Mp: >218° C.

IR (KBr): 1765, 1708 cm$^{-1}$ $^1$H-NMR (CDCl$_3$): δ 7.10-7.75 (m, 8H), 6.50-7.20 (m, 4H), 6.25 (s, 1H), 3.00 (s, 3H), 2.70 (s, 3H)

Example 1: Use of 9-Phenylanthracene Adduct (DAP-PA)

[Triazolinedione Adduct Heating Step]

To 10 mL of ethyl acetate was added 5.00 mg (0.0106 mmol) of 9-phenylanthracene adduct (DAP-PA) obtained in Production Example 1, and the mixture was heated at 80° C. for 30 minutes to prepare an ethyl acetate solution. The color of the ethyl acetate solution turned from colorless to light reddish violet.

[Ene Compound Formation Step]

To 10 mL of the ethyl acetate solution obtained in the triazolinedione adduct heating step was added 0.400 mg (0.00104 mmol) of vitamin D3, and the reaction was allowed to proceed at 25° C. for 1 hour.

[Ene Compound Analysis Step]

Subsequently, the ethyl acetate solution obtained after the ene compound formation step was analyzed using high performance liquid chromatography (HPLC) under the following analytical conditions.

[Analytical Conditions for High Performance Liquid Chromatography]

Column: Inertsil ODS-3 (5 μm, 4.6×250 mm) (manufactured by GL Sciences Inc.)

Detector: ultraviolet-visible spectrometric detector (2489 manufactured by Waters Corporation)

Detection wavelength: 210 nm

Eluent: mobile phase A: acetonitrile

Mobile phase B: distilled water

Mobile phase A/mobile phase B=50/50 (0 to 10 min)

Mobile phase A/mobile phase B=50/50→95/5 (10 to 20 min)

Mobile phase A/mobile phase B=95/5 (20 to 50 min)

Mobile phase A/mobile phase B=95/5→50/50 (50 to 55 min)

Mobile phase A/mobile phase B=50/50 (55 to 60 min)

Flow rate: 1.0 mL/min

Sample temperature: 25° C.

Column temperature: 35° C.

Injection volume: 10 μL

Dilution solvent: acetonitrile

Retention time: DAPTAD-VD3 21.4 min

The analysis revealed that 0.615 mg of a vitamin D3 adduct (DAPTAD-VD3) which is the ene compound represented by the following chemical formula, i.e., (5S,7S)-2-[4-(dimethylamino)phenyl]-5-[(E)-[(1R,3aS,7aR)-1-[(1R)-1,5-dimethylhexyl]octahydro-7a-methyl-4H-inden-4-ylidene]methyl]-5,6,7,8,9,10-hexahydro-7-hydroxy-1H-[1,2,4]triazolo[1,2-b]phthalazine-1,3(2H)-dione was contained. In addition, the recovery rate in terms of vitamin D3 was 98.1%.

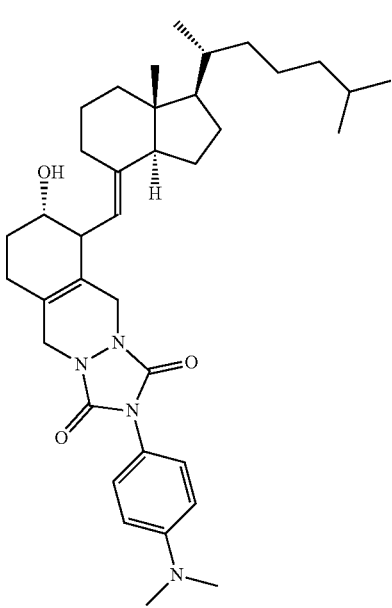

DAPTAD-VD3

The operations executed in Examples and the analysis results etc. are shown in Tables 1 and 2.

TABLE 1

|  | Example 1 | Example 2 | Example 3 | Example 4 |
|---|---|---|---|---|
| Triazolinedione adduct | DAP-PA | DAP-DPA | DAP-MA | DAP-DPA |
| Diene compound | VD3 | VD3 | VD3 | VD3 |
| Heating step: Solvent | Ethyl acetate | Ethyl acetate | Toluene | Ethyl acetate |
| Heating step: Temperature (° C.) | 80 | 70 | 120 | 45 |
| Heating step: Reaction time period | 30 min | 15 min | 2 h | 1 h |
| Triazolinedione adduct concentration | 5 mg/ 10 mL | 10 mg/ 10 mL | 41 mg/ 10 mL | 10 mg/ 10 mL |
| Molar ratio (triazolinedione compound/diene compound) | 10 | 10 | 10 | 18 |
| Ene compound formation step: Temperature (° C.) | 25 | 30 | 20 | 15 |
| Ene compound formation step: Reaction time period | 1 h | 1 h | 30 min | 1 h |
| Recovery rate (%) | 98.1 | 95.2 | 87.1 | 70.3 |
| Ene compound analysis method | HPLC | HPLC | HPLC | HPLC |

TABLE 2

|  | Example 5 | Example 6 | Example 7 | Example 8 |
|---|---|---|---|---|
| Triazolinedione adduct | DAP-PA | DAP-PA | DAP-PA | DAP-PA |
| Diene compound | VD3 | VD3 | VD3 | VD3 |
| Heating step: Solvent | Ethyl acetate | Toluene | Toluene | Ethyl acetate |
| Heating step: Temperature (° C.) | 60 | 100 | 110 | 75 |
| Heating step: Reaction time period | 1 h | 30 min | 30 min | 30 min |
| Triazolinedione adduct concentration | 10 mg/ 100 mL | 5 mg/ 10 mL | 5 mg/ 10 mL | 5 mg/ 10 mL |
| Molar ratio (triazolinedione compound/diene compound) | 815 | 102 | 102 | 8154 |
| Ene compound formation step: Temperature (° C.) | 25 | 30 | 10 | 30 |
| Ene compound formation step: Reaction time period | 1 h | 1 h | 1 h | 1 h |
| Recovery rate (%) | 91.3 | 93.2 | 90.2 | 96.4 |
| Ene compound analysis method | LC-MS | HPLC | HPLC | LC-MS |

Example 2: Use of 9,10-Diphenylanthracene Adduct (DAP-DPA)

[Triazolinedione Adduct Heating Step]

To 10 mL of ethyl acetate was added 10.0 mg (0.0182 mmol) of the 9,10-diphenylanthracene adduct (DAP-DPA) obtained in Production Example 2, and the mixture was heated at 70° C. for 15 minutes to prepare an ethyl acetate solution. The color of the ethyl acetate solution turned to light reddish violet.

[Ene Compound Formation Step]

To 10 mL of the ethyl acetate solution obtained in the triazolinedione adduct heating step was added 0.700 mg (0.00182 mmol) of vitamin D3, and the reaction was allowed to proceed at 30° C. for 1 hour.

[Ene Compound Analysis Step]

Subsequently, the ethyl acetate solution obtained after the ene compound formation step was analyzed using high performance liquid chromatography (HPLC) under analytical conditions identical to those in Example 1.

The analysis revealed that 10.4 mg of a vitamin D3 adduct (DAPTAD-VD3) which is an ene compound was contained. In addition, the recovery rate in terms of vitamin D3 was 95.2%.

Example 3: Use of 9-Methylanthracene Adduct (DAP-MA)

[Triazolinedione Adduct Heating Step]

To 10 mL of toluene was added 41.0 mg (0.100 mmol) of the 9-methylanthracene adduct (DAP-MA) obtained in Production Example 3, and the mixture was heated at 120° C. for 2 hours, to prepare a toluene solution. The color of the solution turned to light reddish violet.

[Ene Compound Formation Step]

To 10 mL of the toluene solution obtained in the triazolinedione adduct heating step was added 3.84 mg (0.0100 mmol) of vitamin D3, and the reaction was allowed to proceed at 20° C. for 30 minutes.

[Ene Compound Analysis Step]

Subsequently, the toluene solution obtained after the ene compound formation step was analyzed using high performance liquid chromatography (HPLC) under analytical conditions identical to those in Example 1.

The analysis revealed that 5.24 mg of a vitamin D3 adduct (DAPTAD-VD3) which is an ene compound was contained. In addition, the recovery rate in terms of vitamin D3 was 87.1%.

Example 4: Use of 9,10-Diphenylanthracene Adduct (DAP-DPA)

[Triazolinedione Adduct Heating Step]

To 10 mL of ethyl acetate was added 10.0 mg (0.0182 mmol) of the 9,10-diphenylanthracene adduct (DAP-DPA) obtained in Production Example 2, and the mixture was heated at 45° C. for 1 hour, to prepare an ethyl acetate solution. The color of the solution turned to light reddish violet.

[Ene Compound Formation Step]

To 10 mL of the ethyl acetate solution obtained in the triazolinedione adduct heating step was added 0.4 mg (0.00104 mmol) of vitamin D3, and the reaction was allowed to proceed at 15° C. for 1 hour.

[Ene Compound Analysis Step]

The ethyl acetate solution obtained after the ene compound formation step was analyzed using high performance liquid chromatography (HPLC) under analytical conditions identical to those in Example 1.

The analysis revealed that 0.440 mg of a vitamin D3 adduct (DAPTAD-VD3) which is an ene compound was contained. In addition, the recovery rate in terms of vitamin D3 was 70.3%.

Example 5: Use of 9-Phenylanthracene Adduct (DAP-PA)

[Triazolinedione Adduct Heating Step]

To 100 mL of ethyl acetate was added 10 mg (0.0212 mmol) of the 9-phenylanthracene adduct (DAP-PA) obtained in Production Example 1, and the mixture was heated at 60° C. for 1 hour, to prepare an ethyl acetate solution. The color of the solution turned to light reddish violet.

[Ene Compound Formation Step]

Into 100 mL of ethyl acetate was dissolved 1.00 mg (0.00260 mmol) of vitamin D3 to prepare a vitamin D3 solution. Subsequently, 1 mL (0.0000260 mmol) of the vitamin D3 solution was added to 100 mL of the ethyl acetate solution obtained in the triazolinedione adduct heating step, and the reaction was allowed to proceed at 25° C. for 1 hour.

[Ene Compound Analysis Step]

The ethyl acetate solution obtained after the ene compound formation step was analyzed using a high performance liquid chromatography-mass spectrometry apparatus (LC-MS) under the following analytical conditions.

[Analytical Conditions for LC-MS]
(Apparatus)
  LC: ACQUITY UPLC (manufactured by Waters Corporation)
  MS: Xevo QTof MS (manufactured by Waters Corporation)
(LC Conditions)
The conditions were identical to the high performance liquid chromatography conditions described in Example 1.
(MS Conditions)
  Source temperature: 120° C.
  Cone gas: 50 L/h
  Solvent-removing temperature: 500° C.
  Solvent-removing gas: 1000 L/h
(Positive)
  Capillary voltage: 3.0 kV
  Sample cone voltage: 20 V The analysis revealed that 0.0143 mg of a vitamin D3 adduct (DAPTAD-VD3) which is an ene compound was contained. In addition, the recovery rate in terms of vitamin D3 was 91.3%.

Example 6: Use of 9-Phenylanthracene Adduct (DAP-PA)

[Triazolinedione Adduct Heating Step]

To 10 mL of toluene was added 5.00 mg (0.106 mmol) of the 9-phenylanthracene adduct (DAP-PA) obtained in Production Example 1, and the mixture was heated at 100° C. for 30 minutes, to prepare a toluene solution. The color of the solution turned to light reddish violet.

[Ene Compound Formation Step]

To 10 mL of the toluene solution obtained in the triazolinedione adduct heating step was added 0.400 mg (0.00104 mmol) of vitamin D3, and the reaction was allowed to proceed at 30° C. for 1 hour.

[Ene Compound Analysis Step]

The toluene solution obtained after the ene compound formation step was analyzed using high performance liquid chromatography (HPLC) under analytical conditions identical to those in Example 1.

The analysis revealed that 0.610 mg of a vitamin D3 adduct (DAPTAD-VD3) which is an ene compound was contained. In addition, the recovery rate in terms of vitamin D3 was 93.2%.

Example 7: Use of 9-Phenylanthracene Adduct (DAP-PA)

[Triazolinedione Adduct Heating Step]

To 10 mL of toluene was added 5.00 mg (0.106 mmol) of the 9-phenylanthracene adduct (DAP-PA) obtained in Production Example 1, and the mixture was heated at 110° C. for 30 minutes, to prepare a toluene solution. The color of the solution turned to light reddish violet.

[Ene Compound Formation Step]

To 10 mL of the toluene solution obtained in the triazolinedione adduct heating step was added 0.400 mg (0.00104 mmol) of vitamin D3, and the reaction was allowed to proceed at 10° C. for 1 hour.

[Ene Compound Analysis Step]

The toluene solution obtained after the ene compound formation step was analyzed using high performance liquid chromatography (HPLC) under analytical conditions identical to those in Example 1.

The analysis revealed that 0.565 mg of a vitamin D3 adduct (DAPTAD-VD3) which is an ene compound was contained. In addition, the recovery rate in terms of vitamin D3 was 90.2%.

Example 8: Use of 9-Phenylanthracene Adduct (DAP-PA)

[Triazolinedione Adduct Heating Step]

To 10 mL of ethyl acetate was added 5.00 mg (0.0106 mmol) of the 9-phenylanthracene adduct (DAP-PA) obtained in Production Example 1, and the mixture was heated at 75° C. for 30 minutes, to prepare an ethyl acetate solution. The color of the solution turned to light reddish violet.

[Ene Compound Formation Step]

Into 100 mL of ethyl acetate was dissolved 0.500 mg (0.00130 mmol) of vitamin D3 to prepare a vitamin D3 solution. Subsequently, 1 mL of the vitamin D3 solution was measured off, and ethyl acetate was added thereto to prepare 10 mL of a diluted vitamin D3 solution.

To 10 mL of the ethyl acetate solution obtained in the triazolinedione adduct heating step was added 1 mL (0.00000130 mmol) of the diluted vitamin D3 solution obtained as described above, and the reaction was allowed to proceed at 30° C. for 1 hour.

[Ene Compound Analysis Step]

The ethyl acetate solution obtained after the ene compound formation step was analyzed using a high performance liquid chromatography-mass spectrometry apparatus (LC-MS) under analytical conditions identical to those in Example 5.

The analysis revealed that 0.00754 mg of a vitamin D3 adduct (DAPTAD-VD3) which is an ene compound was contained. In addition, the recovery rate in terms of vitamin D3 was 96.4%.

What is claimed is:

1. A method for quantifying a diene compound, comprising:
   a triazolinedione adduct heating step of heating a triazolinedione adduct represented by formula (1) to produce a triazolinedione compound represented by formula (2);
   an ene compound formation step of reacting the triazolinedione compound with a diene compound represented by formula (3) to obtain an ene compound represented by formula (4); and
   an ene compound quantifying step of quantifying the ene compound to quantify the diene compound,

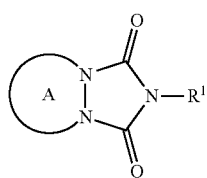

(1)

wherein in the formula (1), $R^1$ represents an organic group; and A represents a fused ring having three or more rings comprising at least one aromatic ring,

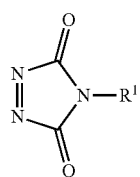

(2)

wherein in the formula (2), $R^1$ is as defined in the formula (1),

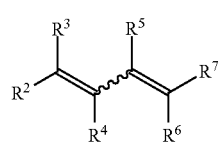

(3)

wherein in the formula (3), $R^2$, $R^3$, $R^4$, $R^5$, $R^6$, and $R^7$ each independently represent a group selected from the group consisting of a hydrogen atom, an alkyl group having 1 to 100 carbon atoms, an aralkyl group, a phenyl group, and a heterocyclic group, wherein the alkyl group, the aralkyl group, the phenyl group, and the heterocyclic group optionally comprise an atom selected from the group consisting of an oxygen atom, a nitrogen atom, a sulfur atom, and a phosphorus atom, and wherein two or more of $R^2$, $R^3$, $R^4$, $R^5$, $R^6$, and $R^7$ are optionally combined with one another, and

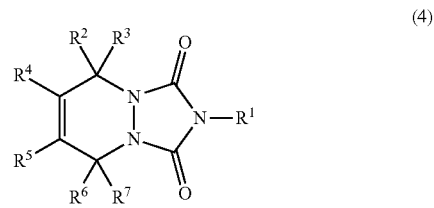

(4)

wherein in the formula (4), $R^1$ is as defined in the formula (1); and $R^2$, $R^3$, $R^4$, $R^5$, $R^6$, and $R^7$ are as defined in the formula (3).

2. The method for analyzing a diene compound according to claim 1, wherein $R^1$ in the formula (1) represents a substituted or unsubstituted phenyl group.

3. The method for analyzing a diene compound according to claim 1, wherein $R^1$ in the formula (1) represents a phenyl group comprising an alkylamino group or an alkylaminoalkyl group.

4. The method for analyzing a diene compound according to claim 1, wherein $R^1$ in the formula (1) represents a phenyl group comprising a dialkylamino group or a dialkylaminoalkyl group.

5. The method for analyzing a diene compound according to claim 1, wherein the triazolinedione adduct represented by the formula (1) is a triazolinedione adduct represented by formula (5):

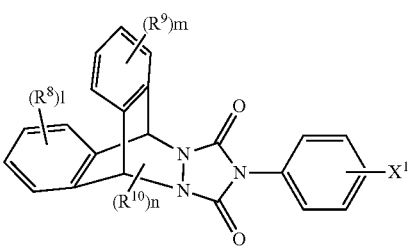

(5)

wherein in the formula (5), $X^1$ represents an organic group; $R^8$, $R^9$, and $R^{10}$ each independently represent a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group; l and m are each independently an integer of 0 to 4; and when $R^{10}$ is an optionally substituted phenyl group, n is an integer of 0 to 1, and when $R^{10}$ is a substituent selected from the group consisting of an optionally substituted alkyl group having 1 to 20 carbon atoms, an optionally substituted aralkyl group, an optionally substituted alkenyl group, an optionally substituted acyl group, a halogen group, an optionally substituted amino group, a nitro group, and an optionally substituted heterocyclic group, n is an integer of 0 to 2.

6. The method for analyzing a diene compound according to claim 5, wherein $X^1$ in the formula (5) represents an alkylamino group or an alkylaminoalkyl group.

7. The method for analyzing a diene compound according to claim 5, wherein $X^1$ in the formula (5) represents a dialkylamino group or a dialkylaminoalkyl group.

8. The method for analyzing a diene compound according to claim 1, wherein the triazolinedione adduct represented by the formula (1) is a triazolinedione adduct represented by formula (6):

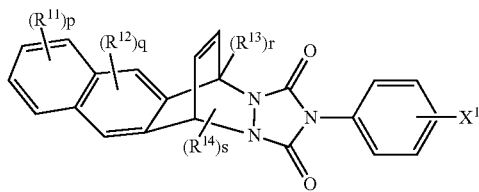
(6)

wherein in the formula (6), $X^1$ represents an organic group; $R^{11}$, $R^{13}$, and $R^{14}$ each independently represent a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group; $R^{12}$ is an optionally substituted phenyl group; p is an integer of 0 to 4; q is an integer of 2; and r and s are each 0 or 1.

9. The method for analyzing a diene compound according to claim 8, wherein $X^1$ in the formula (6) represents an alkylamino group or an alkylaminoalkyl group.

10. The method for analyzing a diene compound according to claim 8, wherein $X^1$ in the formula (6) represents a dialkylamino group or a dialkylaminoalkyl group.

11. The method for analyzing a diene compound according to claim 1, wherein the diene compound is a vitamin.

12. The method for analyzing a diene compound according to claim 11, wherein the vitamin is at least one selected from the group consisting of vitamin D3, 25-hydroxyvitamin D3, 3-epi-25-hydroxyvitamin D3, 24R,25-dihydroxyvitamin D3, vitamin D2, and vitamin A.

13. The method for analyzing a diene compound according to claim 1, wherein a temperature for the heating in the triazolinedione adduct heating step is 50° C. to 100° C.

14. The method for analyzing a diene compound according to claim 1, wherein the analysis in the ene compound quantifying step is performed by a method using at least one selected from the group consisting of high performance liquid chromatography, high performance liquid chromatography-mass spectrometry (LC-MS), high performance liquid chromatography-tandem mass spectrometry (LC-MS/MS), and mass spectrometry.

* * * * *